United States Patent [19]

Barberet et al.

[11] Patent Number: Plant 5,787

[45] Date of Patent: Aug. 26, 1986

[54] CARNATION NAMED LONSEVA

[75] Inventors: Nicole Barberet; Yves Ducloux, both of Antibes, France

[73] Assignee: Laboratoire de Physiologie Vegetale de la Londe, La Londe, France

[21] Appl. No.: 613,713

[22] Filed: May 24, 1984

[51] Int. Cl.[4] ..... A01H 5/00

[52] U.S. Cl. ..... Plt./71

[58] Field of Search ..... Plt./71

*Primary Examiner*—James R. Feyrer

*Attorney, Agent, or Firm*—Charles W. Rummler; John B. Lungmus

[57] ABSTRACT

A new carnation cultivar distinguished by its profuse production of light pink, medium sized blooms carried on long, stiff stems, its vigorous, upright growth habit with moderately abundant foliage, and by its resistance to *Fusarium oxysporum.*

1 Drawing Figure

BACKGROUND OF THE NEW PLANT

This new carnation variety was developed by us at our production facilities at La Londe-Les Maures-Var, France, as a seedling resulting from the cross of two unnamed and unpatented carnation varieties maintained in our collection for breeding purposes. This seedling was selected for propagation and test because of its apparently vigorous growth habit and its beautiful light pink bloom of medium size. The object of this crossing was to produce a strong plant, the flowers of which would have a very attractive form and coloration carried on long, strong stems, and at the same time, have a good resistance to *Fusarium oxysporum.* Reproduction of this seedling was done at La Londe by means of cuttings and successive generations of this plant have demonstrated that the novel characteristics of the parent are retained from generation to generation and appear to be firmly fixed.

DESCRIPTION OF THE DRAWINGS

Our new variety of carnation plant is illustrated by the accompanying photographic drawings which show the color characteristics of the flower as nearly true as it is reasonably possible to obtain by conventional commercial photographic procedures, the view showing buds in several stages of opening, as well as fully developed flowers.

DESCRIPTION OF THE NEW PLANT

The following is a detailed description of our new carnation cultivar as observed in the Fall of 1983, with color designations according to The R.H.S. Colour Chart published by The Royal Horticultural Society at London, England.

THE PLANT

Origin: Seedling.

Parentage:

*Seed parent.*—Carnation No. 9 P 13;

*Pollen parent.*—Carnation No. 73 R 19; as identified in our records of breeding plants maintained by us at La Londe.

Classification:

*Botanic.*—*Dianthus caryophyllus.*

*Commercial.*—Standard carnation.

Form: Bush of erect shape with at least four stems emitted near the ground.

Height: About 100 cm. at ten months.

Growth: Vigorous and upright, with strong, stiff stems and a few branches.

Pinching requirement: On main axis between the 4th and 6th nodes from the base.

Foliage:

*Quantity.*—Moderately abundant with more than 120 leaves.

*Leaf size.*—Averaging about 16 cm. long and about 1.1 cm. wide.

*Leaf shape.*—Linear with acute apex and rolled margin, taken at the seventh node.

*Texture.*—Leathery.

*Color.*—Upper side — 189A. Under Side — 189A.

*Ribs and veins.*—Hardly noticeable.

*Rachis.*—Hardly noticeable.

*Petioles.*—None. The leaf is amplexicaul.

THE BUD

Form: Ovoid.

Size: Medium.

*Diameter.*—About 2.3 cm. in average.

*Length.*—About 3.8 cm. in average.

Rate of opening: About Normal.

Color of petals:

*When sepals first divide and when petals begin to unfurl.*—Same as at full bloom.

Sepals:

*Number.*—Five.

*Character.*—Hooded over the bud and upstanding when flowers open.

*Color.*—Inside — Greenish. Outside — 143B.

*Striae.*—Apparent.

Calyx:

*Size.*—Large, broad and of medium length.

*Shape.*—Urn-shaped and relatively short.

*Splitting.*—The calyx very rarely splits.

Flower stem:

*Length.*—About 80 cm.

*Strength.*—Erect and rigid.

*Color.*—R.H.S. 189A.

THE FLOWER

Blooming habit: Profuse and recurrent the year around.

Size of bloom: Medium; diameter averaging 8.3 cm., depth averaging about 6 cm.

Borne: Singly, terminal of each floral stem.

Shape:

*When bloom first opens.*—High centered.

*When bloom matures.*—Ball-shaped.

Petalage:

*Number of petals.*—Averaging about 54.

*Arrangement.*—Imbricated.

*Form.*—Fan-shaped with rounded side edges and serrated at the apex margin.

*Texture.*—Soft.

*Appearance.*—Satiny.

*Color.*—Outside and Inside Petals: Body — 55C-D. Base — Greenish. Reverse side — 55D.

*Petaloids.*—None.

*Persistence.*—Petals hang on and dry.

Fragrance: Hardly perceptible.

Disease resistance: This plant is rather tolerant to *Fusarium oxysporum* as observed at La Londe and at Antibes, France.

Lasting quality: Good, and at least ten days as a cut flower.

REPRODUCTIVE ORGANS

Stamens:

*Number.*—In average, ten.

*Arrangement.*—Around the ovary.

*Anthers.*—Size: Less than 4 mm. Color: Whitish.

*Filaments.*—Color: Lightly pinkish.

Pistils:

*Number.*—Mostly four.

*Styles.*—Color: Lightly pinkish.

*Stigmas.*—Color: Lightly pinkish.

Character of ovaries: Ribbed.

This new carnation cultivar most nearly resembles the variety "Baranna" (U.S. Plant Pat. No. 3,534) and compared with "Baranna" and "Barlo II" (U.S. Plant Pat. No. 3,406), the blossom of the new plant has rather deeply serrated petals, a stiffer stem, and an intermediate color. Also, this new variety is more tolerant to *Fusarium oxysporum* than the others referred to.

We claim:

1. A new and distinct carnation cultivar, substantially as herein shown and described, characterized in particular by its light pink, medium sized blooms of full shape carried on rather long, stiff stems.

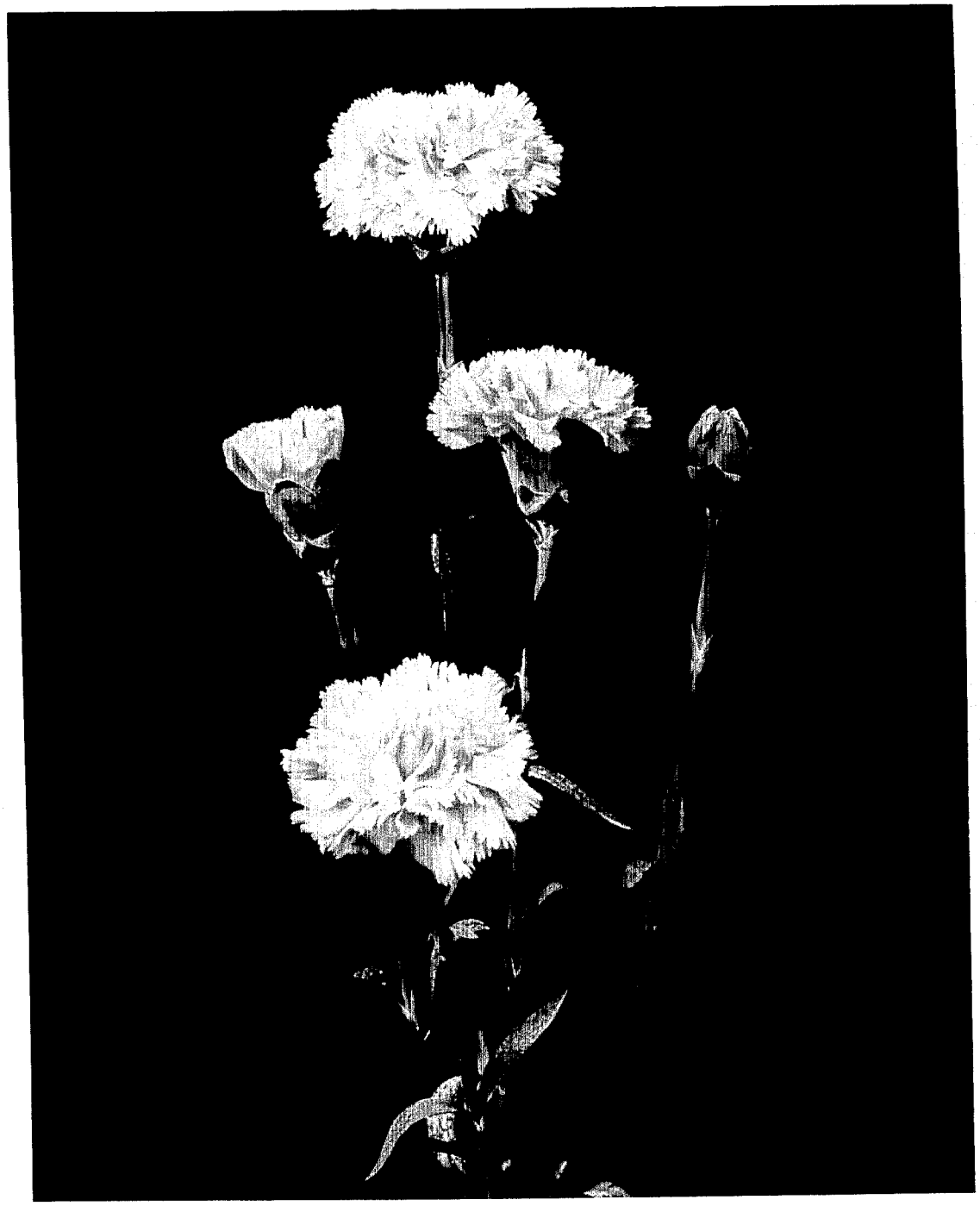

* * * * *